United States Patent [19]

Sachtler et al.

[11] Patent Number: 4,874,731
[45] Date of Patent: Oct. 17, 1989

[54] CATALYST FOR THE ISOMERIZATION OF AROMATICS

[75] Inventors: J. W. Adriaan Sachtler, Des Plaines; R. Joe Lawson, Palatine, both of Ill.

[73] Assignee: UOP, Des Plaines, Ill.

[21] Appl. No.: 107,604

[22] Filed: Oct. 13, 1987

[51] Int. Cl.$^4$ .................. B01J 29/32; B01J 29/36
[52] U.S. Cl. ........................... 502/66; 502/61; 502/71
[58] Field of Search ............... 502/71, 77, 66; 585/481

[56] References Cited

U.S. PATENT DOCUMENTS

| | | | |
|---|---|---|---|
| 3,417,157 | 12/1968 | Pollitzer | 260/672 |
| 3,527,824 | 9/1970 | Pollitzer | 260/672 |
| 3,527,825 | 9/1970 | Pollitzer | 260/672 |
| 3,583,903 | 6/1971 | Miale et al. | 502/78 |
| 3,855,115 | 12/1974 | Morrison | 502/77 |
| 3,871,993 | 3/1975 | Morrison | 502/71 |
| 3,953,366 | 4/1976 | Morrison | 252/455 Z |
| 4,080,396 | 3/1978 | Butter | 502/77 |
| 4,236,996 | 12/1980 | Tabak et al. | 585/481 |
| 4,304,657 | 12/1981 | Miller | 208/135 |
| 4,482,773 | 11/1984 | Chu et al. | 585/481 |
| 4,485,185 | 11/1984 | Onodera et al. | 502/71 |

FOREIGN PATENT DOCUMENTS 108246 8/1975 Japan .................. 585/481

Primary Examiner—Carl F. Dees
Attorney, Agent, or Firm—Thomas K. McBride; John F. Spears, Jr.

[57] ABSTRACT

An improved catalyst for the isomerization of non-equilibrium $C_8$ aromatics is presented which utilizes a novel catalytic composition. This catalyst comprises a Group VIII metal component, a bismuth component, and crystalline aluminosilicate zeolite having a silica to alumina ratio of at least 12. An isomerization process is also disclosed which has a particular utility for the conversion of ethylbenzene without the deleterious loss of xylene.

8 Claims, 1 Drawing Sheet

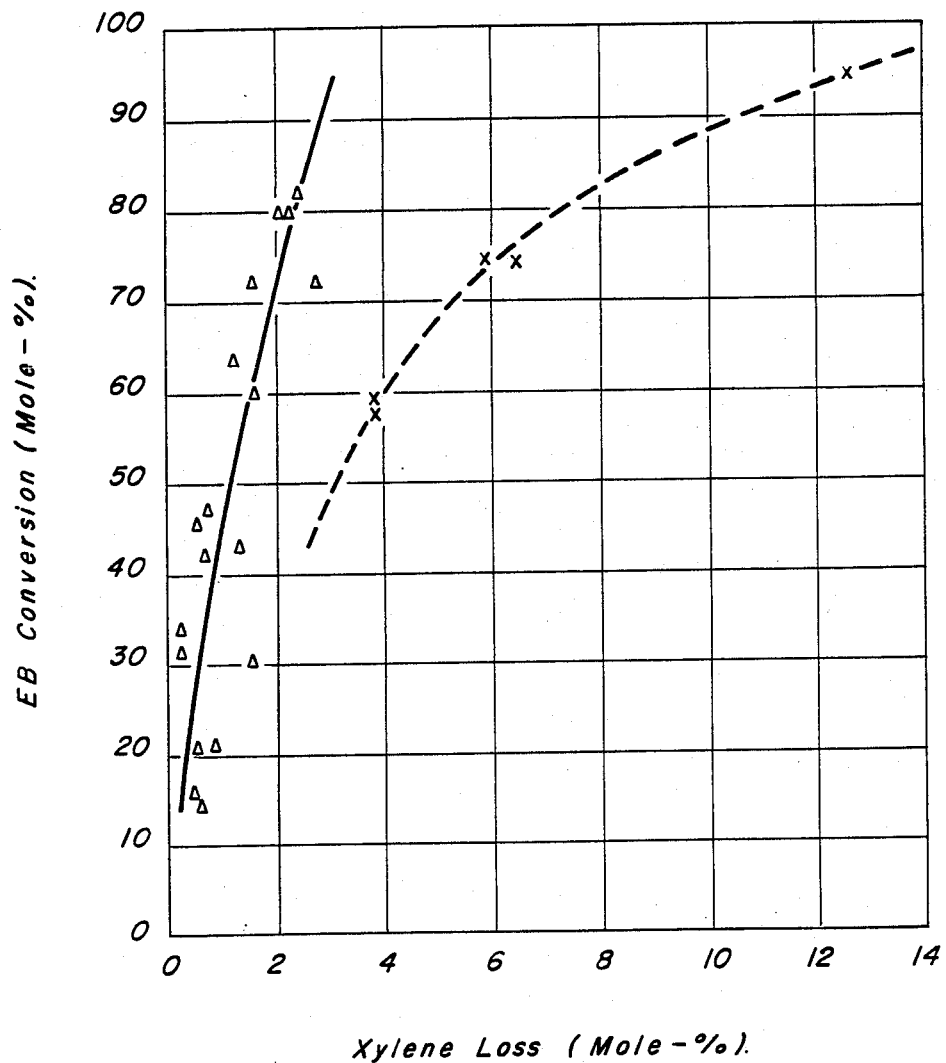

CATALYST FOR THE ISOMERIZATION OF AROMATICS

BACKGROUND OF THE INVENTION

This invention relates to an improved catalyst useful for the catalytic isomerization of xylenes and conversion of ethylbenzene. More specifically, it relates to a catalyst composition comprising a crystalline aluminosilicate zeolite, a bismuth component, a Group VIII metal component, and an inorganic oxide matrix.

Isomerization of xylenes is industrially performed by the steps, in suitable combinations, of isomerizing an aromatic hydrocarbon feedstock containing mainly xylene isomers, separating a specified xylene isomer, normally para-xylene, from the resulting isomerization reaction mixture, and recycling the mixture left after separation. It is industrially significant in this case, for an increased efficiency of the isomerization reaction and a reduced cost of production, to adjust the composition of the xylene isomers in the isomerization reaction product as closely as possible to the thermodynamic equilibrium composition, and to inhibit side-reactions such as the decomposition of xylenes (particularly, by hydrogenation of the benzene ring, dealkylation of a methyl group, and transalkylation).

Many methods for isomerizing xylenes have been suggested in the past and many of them involve the use of a crystalline aluminosilicate zeolite-containing catalyst. Crystalline aluminosilicates generally referred to as zeolites, may be represented by the empirical formula:

$$M_{2/n}O \cdot Al_2O_3 \cdot xSiO_2 \cdot yH_2O$$

in which n is the valence of M which is generally an element of Group I or II, in particular, sodium, potassium, magnesium, calcium, strontium, or barium, and x is generally equal to or greater than 2. Zeolites have skeletal structures which are made up of three-dimensional networks of $SiO_4$ and $AlO_4$ tetrahedra, corner linked to each other by shared oxygen atoms. The greater the proportion of the $SiO_4$ species to the $AlO_4$ species, the better suited the zeolite is for use as a component in isomerization catalysts. Representative zeolites having such high proportion of $SiO_4$ include mordenite and the ZSM variety. In addition to the zeolite component, certain metal promoters and inorganic oxide matrices have been included in isomerization catalyst formulations. Examples of inorganic oxides include silica, alumina, and mixtures thereof. Metal promoters such as Group VIII or Group III metals of the Periodic Table, have been used to provide a dehydrogenation functionality. The acidic function can be supplied by the inorganic oxide matrix, the zeolite, or both.

A commercially viable isomerization process is one that concurrently meets the following objectives. First, the process must exhibit high xylene isomerization activity and, second, it must produce the desired product without a significant loss of xylenes. This loss is a result of undesired side-reactions, involving hydrogenation of the aromatic ring, hydrogenolysis, demethylation, and particularly disproportionation and transalkylation.

Another factor of importance in a xylene isomerization process is the effect that ethylbenzene has on the entire isomerization and xylene recovery loop. When ethylbenzene, which is normally present in 8 carbon atom aromatic fractions, is present in appreciable quantities in the feed to the isomerization process, it will accumulate in the loop unless it is excluded from the feed or converted by some reaction in the loop to products which are separable from xylenes by means tolerable in the loop. Ethylbenzene can be separated from the xylenes of boiling point near that of ethylbenzene by extremely expensive "superfractionation". A more desirable method of eliminating the ethylbenzene is through a conversion reaction taking place simultaneously with the isomerization reaction of the xylenes. It is preferable that this ethylbenzene conversion reaction be a deethylation reaction producing benzene and ethane rather than a disproportionation reaction to benzene and diethylbenzene. The deethylation reaction preserves more xylenes and produces a high quality benzene-containing reaction product.

It has now been found that, if a catalyst is formulated with the components, and in the manner set forth hereinafter, an improved process for the isomerization of non-equilibrium mixed xylenes containing ethylbenzene is obtained.

OBJECTS AND EMBODIMENTS

A principal object of the present invention is to provide a novel hydrocarbon conversion catalyst for the isomerization of aromatic hydrocarbons and an improved process for employing same. Further, the use of this catalyst results specifically in improved conversion of ethylbenzene with the added benefit of an exceptionally high retention of xylenes. Other objects in applying embodiments of the instant invention include providing an efficient and effective catalyst manufacturing procedure. Accordingly, a broad embodiment of the present invention is directed toward a catalyst useful for isomerizing isomerizable alkylaromatic hydrocarbons comprising a pentasil zeolite, a Group VIII metal component, a bismuth component, and an inorganic oxide binder. Other embodiments are directed toward a method of manufacture of this catalyst and toward an isomerization process utilizing a catalyst useful for isomerizing isomerizable alkylaromatic hydrocarbons comprising a pentasil zeolite, a Group VIII metal component, a bismuth component, and an inorganic oxide binder.

INFORMATION DISCLOSURE

The prior art is replete with references relating to hydrocarbon conversion catalysts that have utility in alkylaromatic isomerization processes. However, it is believed that none of the prior references recognizes the catalyst composition of the instant invention nor its use in an isomerization process. Of some relevance to the instant invention are U.S. Pat. Nos. 3,527,824 (Pollitzer); 3,953,366 (Morrison); and 4,304,657 (Miller).

The Pollitzer patent teaches a transalkylation process utilizing a catalyst containing a crystalline aluminosilicate, a Group VIII metal, and an additional component selected from a list of five metals, in which bismuth is included. This reference teaches only the use of either mordenite or faujasite and is completely silent to the utility of a pentasil zeolite.

The Morrison and Miller references are similar in that they are both directed to an aromatization process which converts light hydrocarbons, $C_2$–$C_4$, to aromatic hydrocarbons. Both references recognize the utility of a pentasil zeolite, however, neither is cognizant of the unique combination of catalytic elements found in the catalyst composition of the instant invention. Likewise, neither recognize the applicability to an isomerization process.

While the above-noted prior art is considered of interest in connection with the subject matter of the present invention, the unique combination of catalytic components and process use thereof has not, insofar as is known been previously described.

DETAILED DESCRIPTION OF THE INVENTION

This invention is concerned with the catalytic isomerization and conversion of a non-equilibrium mixture of $C_8$ aromatic hydrocarbons utilizing a novel catalytic composition comprising a pentasil zeolite, a Group VIII metal component, a bismuth component, and an inorganic oxide binder. It has been found, surprisingly and unexpectedly, that the instant catalyst when used in an isomerization process converts more ethylbenzene and preserves more aromatics than conventional isomerization catalysts of the prior art.

As mentioned, the catalyst of the instant invention contains a pentasil zeolite. "Pentasil" is a term used to describe a class of shape-selective zeolites. This novel class of zeolites is well known to the art and is typically characterized by a silica/alumina mole ratio of at least about 12. Descriptions of the pentasils may be found in U.S. Pat. Nos. 4,159,282; 4,163,018; and 4,278,565, all of which are incorporated herein by reference. Of the pentasil zeolites, the preferred ones are ZSM-5, ZSM-8, ZSM-11, ZSM-12, ZSM-23, and ZSM-35, with ZSM-5 being particularly preferred. It is a preferred embodiment of the present invention that the pentasil be in the hydrogen form. Conversion of an alkali metal form pentasil to the hydrogen form may be performed by treatment with an aqueous solution of a mineral acid. Alternatively, hydrogen ions can be incorporated into the pentasil by ion exchange with ammonium hydroxide followed by calcination. The relative proportions of the pentasil zeolite and the other components of the catalytic composite vary widely with the pentasil zeolite content ranging from about 1 to about 80 wt. % and more preferably ranging from 2 to 60 wt. %.

It is also within the scope of the present invention that the particular pentasil selected may be a gallosilicate. Gallosilicates have essentially the same structure as the ZSM-type zeolites described hereinabove, except that all or part of the aluminum atoms in the aluminosilicate crystal framework are replaced by gallium atoms. This substitution of the aluminum by gallium is usually performed prior to or during synthesis of the zeolite. The gallium content for this particular type of pentasil, expressed as mole ratios of $SiO_2$ to $Ga_2O_3$, ranges from 20:1 to 400:1 or more.

Considering next the inorganic oxide binder utilized in the present invention, it is preferred that the binder be a porous, adsorptive, high-surface area support having a surface area of about 25 to about 500 m$^2$/g. The binder should also be uniform in composition and relatively refractory to the conditions utilized in the hydrocarbon conversion process. By the term "uniform in composition", it is meant that the support be unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention binder materials which have traditionally been utilized in dual-functional hydrocarbon conversion catalysts such as: (1) activated carbon, coke, or charcoal; (2) silica or silica gel, silicon carbide, clays and silicates including those synthetically prepared and naturally occurring, which may or may not be acid treated, for example, attapulgus clay, diatomaceous earth, fuller's earth, kaolin, kieselguhr, etc.; (3) ceramics, porcelain, bauxite; (4) refractory inorganic oxides such as alumina, titanium dioxide, zirconium dioxide, chromium oxide, zinc oxide, magnesia, thoria, boria, silica-alumina, silicamagnesia, chromia-alumina, alumina-boria, silica-zirconia, zirconia-alumina, etc.; and (5) combinations of one or more elements from one or more of these groups. The preferred binders for use in the present invention are refractory inorganic oxides, with best results obtained with a binder comprised of alumina. Suitable aluminas are the crystalline aluminas known as the gamma-, eta-, and theta-aluminas, with gamma-alumina as the preferred form. In addition, in some embodiments, the alumina binder may contain minor proportions of other well known refractory inorganic oxides such as silica, zirconia, magnesia, etc.; however, the preferred binder is substantially pure gamma-alumina. Preferred binders have an apparent bulk density of about 0.3 to about 0.8 g/cc and surface area characteristics such that the average pore diameter is about 20 to 300 angstroms and the pore volume is about 0.1 to about 1 cc/g. In general, excellent results are typically obtained when the binder of the catalyst is gamma-alumina in the form of spherical particles having a relatively small diameter (i.e., typically about 1/16-inch), an apparent bulk density of about 0.6 g/cc, a pore volume of about 0.8 cc/g, and a surface area of about 200–250 m$^2$/g.

The preferred alumina binder is uniform in composition and may be prepared in any suitable manner and may be synthetically prepared or naturally occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina binder may be prepared by adding a suitable alkaline reagent, such as ammonium hydroxide to a salt of aluminum such as aluminum chloride, aluminum nitrate, etc., in an amount to form an aluminum hydroxide gel which, upon drying and calcining, is converted to alumina.

Using techniques commonly known to those skilled in the art, the catalyst of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing. A preferred shape for the catalyst composite is the extrudate prepared using the well-known extrusion method. Here the pentasil zeolite with or without metallic components added is combined with the binder and a suitable peptizing agent and mixed to form a homogeneous dough or thick paste. This material is then extruded through a die pierced with multiple holes and the spaghetti-shaped extrudate is cut off on the opposite side to form short cylinders. The rheological properties of the dough mixture can be varied by the use of "extrusion aids" such as methylcellulose, stearates, small amounts of clay, colloidal silica, etc. After extrusion, the cylinders are dried and calcined as set forth hereinbelow.

For the purposes of the present invention, the most preferred shape of the subject catalytic composite is the sphere, manufactured by the well-known oil drop method which comprises forming a hydrosol of the desired inorganic oxide binder by any of the techniques taught in the art, for example, alumina hydrosol is preferably prepared by reacting aluminum metal with hydrochloric acid. The pentasil zeolite is then uniformly dispersed in the hydrosol. This resultant zeolite-containing hydrosol is then commingled with a suitable gelling agent and is dispersed as droplets into an oil bath maintained at elevated temperatures. As previously mentioned, the bismuth component may be added to the mixture prior to forming the droplets and either before, after, or simultaneously with the pentasil. The droplets of the mixture remain in the oil bath until they set and form hydrogel spheres. The spheres are continuously withdrawn from the oil bath and typically subjected to specific aging treatments in oil and an ammoniacal solution to further improve their physical characteristics. The resulting aged and gelled particles are then washed and dried at a relatively low temperature of about 100°–205° C. and subjected to a calcination procedure at a temperature of about 450°–700° C. for a period of about 1 to about 20 hours. See the teachings of U.S. Pat. No. 2,620,314 for additional details.

Another component of the instant invention is the Group VIII metal. Preferably, this Group VIII metal is selected from the platinum group metals. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum group component exists in the elemental state. The platinum group component generally comprises from about 0.01 to about 5 wt. % of the final catalytic composite, calculated on an elemental basis. It is preferred that the platinum content of the catalyst be between about 0.05 and 3 wt. %. The preferred platinum group component is platinum, with palladium being the next preferred metal. The platinum group component may be incorporated into the catalyst composite in any suitable manner such as by coprecipitation or cogelation with the preferred binder material, or by ion-exchange or impregnation of the zeolite/binder composite. Alternatively, the platinum group metal may be added directly to the zeolite prior to incorporation of the binder. The preferred method of preparing the catalyst normally involves the utilization of a water-soluble, decomposable compound of a platinum group metal to impregnate the calcined zeolite/binder composite. For example, the platinum group component may be added to the calcined hydrogel by commingling the calcined composite with an aqueous solution of chloroplatinic or chloropalladic acid. An acid such as hydrogen chloride is generally added to the impregnation solution to aid in the distribution of the platinum group component through the composite.

Yet another embodiment of the instant invention is the bismuth component. This component may be present as an elemental metal, as a chemical compound such as the oxide, sulfide, halide, oxychloride, etc., or as a physical or chemical combination with the porous binder material and/or other components of the catalytic composite. The bismuth component is preferably utilized in an amount sufficient to result in a final catalytic composite containing about 0.01 to about 5 wt. % bismuth, calculated on an elemental basis, with best results obtained at a level of about 0.1 to about 2 wt. %. The bismuth component may be incorporated in the catalytic composite in any suitable manner to achieve a uniform dispersion such as by coprecipitation or cogelation with the inorganic oxide binder with or without the zeolite, ion-exchange with the inorganic oxide binder, ion exchange with the pentasil, or impregnation of the catalyst at any stage in the preparation. It is to be noted that it is intended to include within the scope of the present invention all conventional methods for incorporating a metallic component in a catalytic composite. One preferred method of incorporating the bismuth component into the catalytic composite involves coprecipitating the bismuth component during the preparation of the preferred inorganic oxide binder. In the preferred case, this involves the addition of suitable soluble bismuth compounds such as bismuth nitrate, bismuth acetate, bismuth trichloride, bismuth tribromide, bismuth trioxide, and the like to a hydrosol of the inorganic oxide, and then combining the hydrosol with a suitable gelling agent and dropping the resulting mixture into an oil bath, etc., as explained in more detail below. After calcining the gelled hydrosol, there is obtained a binder material having a uniform dispersion of bismuth oxide in an intimate combination with the inorganic oxide binder. Another preferred method of incorporating the bismuth component into the catalyst composite involves the utilzation of a soluble, decomposable compound of bismuth to impregnate and uniformly disperse the bismuth throughout the inorganic oxide binder and pentasil zeolite.

The catalyst of this invention finds utility in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Suitable alkylaromatic hydrocarbons include, for example, ortho-xylene, meta-xylene, para-xylene, ethylbenzene, ethyltoluenes, the trimethylbenzenes, the diethylbenzenes, the triethylbenzenes, methylpropylbenzenes, ethylpropylbenzenes, the diisopropylbenzenes, the triisopropylbenzenes, etc., and mixtures thereof. Preferred isomerizable alkylaromatic hydrocarbons include the xylene isomers in admixture with ethylbenzene as a nonequilibrium mixture.

The isomerizable alkylaromatic hydrocarbons may be utilized as found in selective fractions from various refinery petroleum streams, e.g., as individual components or as certain boiling range fractions obtained by the selective fractionation and distillation of catalytically cracked gas oil. The process of this invention may be utilized for conversion of isomerizable aromatic hydrocarbons when they are present in minor quantities in various streams. The isomerizable aromatic hydrocarbons which may be used in the process of this invention need not be concentrated. The process of this invention allows the isomerization of alkylaromatic containing streams such as reformate to produce specified xylene isomers, particularly para-xylene, thus upgrading the reformate from its gasoline value to a high petrochemical value.

According to the process of the present invention, an alkylaromatic hydrocarbon charge stock, preferably in admixture with hydrogen, is contacted with a catalyst of the type hereinbefore described in an alkylaromatic hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of the catalyst previously characterized. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed, while maintaining the zone at proper alkylaromatic isomerization conditions such as a temperature in the range from about 0°–600° C. or more, and a pressure of atmospheric to about 100 atmospheres or more. Preferably, a temperature range of about 350°–500° C. and a pressure range of 5–20 atmospheres is desired. The hydrocarbon is passed into the reaction zone, preferably in admixture with hydrogen, at a hydrogen to hydrocarbon mole ratio of about 0.5:1 to about 25:1 or more, and at a liquid hourly hydrocarbon space velocity of about 0.1 to about 20 $hr^{-1}$ or more, most preferably at 0.5 to 15 $hr^{-1}$. Other inert diluents such as nitrogen, argon, etc., may be present.

The particular product recovery scheme employed is not deemed to be critical to the instant invention. Any recovery scheme known in the art may be used. Typically, the reactor effluent will be condensed with the hydrogen and light hydrocarbon components removed therefrom by flash separation. The condensed liquid product is then subjected to a fractionation procedure to further purify the desired liquid product. In some instances, it may be desirable to recover certain product species, such as ortho-xylene, by selective fractionation. In most instances, the liquid xylene product is processed to selectively recover the para-xylene isomer. Recovery of para-xylene can be performed by crystallization methods or most preferably by selective adsorption using crystalline aluminosilicates.

BRIEF DESCRIPTION OF THE DRAWING

Reference to the accompanying drawing may facilitate understanding of the present invention. The drawing graphically illustrates the relationship between ethylbenzene conversion, expressed as mole percent, and xylene loss, expressed as mole percent destroyed across the isomerization reaction zone.

The following example will serve to illustrate certain specific embodiments of the herein disclosed invention. This example should not, however, be construed as limiting the scope of the invention as set forth in the claims as there are many variations which may be made thereon without departing from the spirit of the invention, as those of ordinary skill in the art will recognize.

EXAMPLE

This example presents test results obtained when the catalyst of the instant invention was evaluated relative to a prior catalyst in an alkylaromatic isomerization process. Each process was evaluated using a pilot plant flow reactor processing a feed comprising approximately 3.5 wt. % p-xylene, 68.4 wt. % m-xylene, 16.8 wt. % o-xylene, 10.3 wt. % ethylbenzene, 0.6 wt. % toluene, and the balance $C_9$ nonaromatics. The operating conditions used in the evaluation tests comprised a range of temperatures from about 390°–475° C., pressures from 5.2 to 15 atmospheres, and liquid hourly space velocities from 4 to 8.1 $hr^{-1}$. The temperature and space velocity were varied over the range stated in order to develop the relationship between ethylbenzene conversion and xylene retention as illustrated in the attached Figure. The pressure is increased or decreased as the temperature is varied in order to prevent an excessive formation of $C_8$ nonaromatic cyclic hydrocarbons, commonly referred to as naphthenes. It is desired to maintain a $C_8$ naphthene to $C_8$ aromatic mole ratio of less than 0.01.

Catalyst A represents a catalyst of the prior art. This catalyst comprised approximately 11 wt. % hydrogen-form ZSM-5 zeolite, 0.29 wt. % platinum, and approximately 89 wt. % $Al_2O_3$ as the binder. Formulation of the catalyst by the oil drop method was as follows. Initially, the zeolite was added to an alumina sol solution, prepared by digesting metallic aluminum in hydrochloric acid, in an amount sufficient to yield a zeolite content in the finished catalyst of about 11 wt. %. A second solution of hexamethylenetetramine (HMT) was prepared and added to the zeolite/alumina sol mixture to give homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C. These calcined spheres were then impregnated with a solution of chloroplatinic acid with 2 wt. % hydrochloric acid to yield a final platinum level of 0.29 wt. % on the finished catalyst. The impregnated spheres were oxidized and chloride adjusted at 525° C. and then subjected to a reducing environment of $H_2$ at 565° C. The isomerization performance results for Catalyst A are presented in the accompanying FIGURE.

Catalyst B was prepared in accordance with the instant invention and had a composition comprising approximately 11 wt. % ZSM-5 zeolite, 0.30 wt. % platinum, 0.34 wt. % bismuth, and approximately 89 wt. % gamma-alumina. The catalyst was prepared by the oil drop method in the same manner as Catalyst A with the bismuth added by impregnation of the calcined zeolite/alumina composite. Also illustrated in the attached FIGURE are the test results for Catalyst B.

In analyzing the performance of the three processes, it is desirable to focus on a particular level of ethylbenzene conversion and then examine to what extent each process preserved valuable xylene product, i.e., had the lowest xylene loss. Picking 60 mol. % ethylbenzene conversion as a basis, it is readily apparent from the FIGURE that the catalyst of the instant invention, Catalyst B, exhibits increased preservation of xylene product compared to the prior art catalyst. In other words, the prior art catalyst, Catalyst A, destroys over twice the amount of xylene compared to the catalyst of the instant invention when converting an equivalent amount of ethylbenzene.

What is claimed is:

1. An isomerization catalyst useful for the isomerization of $C_8$ aromatics and conversion of ethylbenzene comprising 2 to 60 wt. % of a pentasil zeolite, 0.05 to 3 wt. % platinum, 0.1 to 2 wt. % bismuth, and an alumina binder.

2. The catalyst of claim 1 further characterized in that the alumina comprises gamma-alumina.

3. The catalyst of claim 1 further characterized in that the pentasil zeolite is selected from the group consisting of ZSM-5, ZSM-8, ZSM-11, ZSM-12, ZSM-23, and ZSM-35.

4. The catalyst of claim 1 further characterized in that the pentasil zeolite is hydrogen form ZSM-5.

5. The catalyst of claim 1 further characterized in that the pentasil zeolite is a gallosilicate.

6. The catalyst of claim 1 further characterized in that the bismuth component is first intimately admixed with the alumina binder prior to combining the pentasil zeolite.

7. A method of preparing a hydrocarbon conversion catalyst comprising commingling a pentasil zeolite, a platinum component, a bismuth component, and an alumina binder to form a shaped catalyst composite.

8. The catalyst of claim 1 further characterized in that the alumina binder is formed by the oil drop method.

* * * * *